United States Patent [19]
Psaros et al.

[11] Patent Number: 5,765,558
[45] Date of Patent: Jun. 16, 1998

[54] TRACHEAL TUBE AND VENTILATOR SYSTEM PERMITTING ENDOGENOUSLY-PRODUCED NO TO BE COMBINED WITH RESPIRATORY GAS

[75] Inventors: Georgios Psaros, Tullinge; Kurt Högnelid, Bromma, both of Sweden

[73] Assignee: Siemens Elema AB, Solna, Sweden

[21] Appl. No.: 726,669

[22] Filed: Oct. 7, 1996

[30] Foreign Application Priority Data

Oct. 13, 1995 [SE] Sweden ................................. 9503579
Oct. 13, 1995 [SE] Sweden ................................. 9503624

[51] Int. Cl.$^6$ ............................................. A61M 16/00
[52] U.S. Cl. ........................... 128/207.14; 128/207.16; 128/207.18; 128/203.12; 128/203.22; 128/911
[58] Field of Search ..................... 128/207.14, 207.16, 128/207.18, 911, 200.26, 203.22, 204.18, 204.21, 204.23, 203.12, 207.29, 206.11, 201.26, 200.14

[56] References Cited

U.S. PATENT DOCUMENTS

| | | | |
|---|---|---|---|
| 4,778,448 | 10/1988 | Meer | 128/207.18 |
| 4,821,715 | 4/1989 | Downing | 128/200.26 |
| 5,339,808 | 8/1994 | Don Michael | 128/911 |
| 5,396,882 | 3/1995 | Zapol | 128/200.14 |
| 5,471,977 | 12/1995 | Olsson et al. | 128/204.22 |
| 5,522,381 | 6/1996 | Olsson et al. | 128/203.12 |
| 5,531,218 | 7/1996 | Krebs | 128/203.12 |
| 5,544,648 | 8/1996 | Fisher, Jr. | 128/207.14 |
| 5,558,083 | 9/1996 | Bathe et al. | 128/203.12 |

FOREIGN PATENT DOCUMENTS

| | | | |
|---|---|---|---|
| 0 640 357 | 3/1995 | European Pat. Off. | A61M 16/12 |
| WO 92/10228 | 6/1992 | WIPO | A61M 11/00 |
| 9305709 | 4/1993 | WIPO | A61B 5/08 |

*Primary Examiner*—Aaron J. Lewis
*Assistant Examiner*—V. Srivastava
*Attorney, Agent, or Firm*—Hill & Simpson

[57] ABSTRACT

A ventilator system and a tracheal tube, inserted into a patient's trachea to carry gas to and from the lungs, permit a gas mixture containing endogenous NO, which is present in the upper respiratory tract, to be supplied to the lungs. The tracheal tube has a input port which forms a connection between the interior of the tracheal tube and the upper respiratory tract. The input port draws or forces an amount of the gas containing endogenous NO into the tracheal tube and this gas accompanies the respiratory gas into the lungs during inspiration.

23 Claims, 5 Drawing Sheets

TRACHEAL TUBE AND VENTILATOR SYSTEM PERMITTING ENDOGENOUSLY-PRODUCED NO TO BE COMBINED WITH RESPIRATORY GAS

BACKGROUND OF THE INVENTION

1. Field of the Invention

The present invention is directed to a tracheal tube as well as to a ventilator system wherein endogenously-produced nitric oxide (NO) can be combined with respiratory gas.

As used herein, "tracheal tube" includes basically all medical appliances that are used in ventilator/respirator/ anaesthetic systems for connecting a patient to the system, i.e., tubes that are inserted in the trachea through the mouth or nose of the patient as well as tracheotomy and tracheostomy tubes.

2. Description of the Prior Art

PCT Application WO 92/10228 describes, among other things, the benefit of supplying extremely small quantities of NO to a patient's lungs for medical purposes, e.g., to counteract asthma and pulmonary vasoconstriction.

Small quantities of NO are believed to possess other advantageous properties, such as counteracting bacterial and viral attacks on the lungs. Nature itself ensures that humans produce their own NO in e.g., the upper respiratory tract. This endogenous NO is then carried down into the lungs during inhalation and is distributed in the lungs in the most advantageous manner.

On some occasions, however, an individual may be dependent upon the respiration support provided by a ventilator or respirator. The ventilator can support or control the patient's breathing. Ventilators and their operating modes have been well-known for a long time. When respiratory support is provided with a breathing mask on the patient's face, or if respiratory gas is carried to the patient's lungs in some other fashion via the mouth and nose (the upper respiratory tract), endogenous NO gas accompanies the respiratory gas in a natural way.

Problems arise, however, when a tracheal tube is used to carry respiratory gas into the patient's lungs. The upper respiratory tract does not then come into contact with the respiratory gas, and endogenous NO gas remains unmixed therewith. This can lead to certain complications for the patient. For example, pneumonia is common in patients who have been intubated for a long time. The lack of NO in the respiratory gas is viewed as a contributory factor. Assisted breathing, however, is often essential to the patient's life.

External sources of NO gas can be used for supplying small amounts of NO to the respiratory gas and, accordingly, to the patient's lungs, however, a number of problems occur in the use of external sources of No gas. The NO concentration must be kept low, usually from 1 to 100 ppm. At higher concentrations, i.e. more than 150-200 ppm, the risk to the patient increases, since NO reacts strongly, with oxygen, forming $NO_2$, a highly toxic gas.

A number of different devices and methods have been proposed for supplying NO from an external source to a patient's lungs in the safest way possible. These known techniques include supplying NO by exact regulation of extremely small gas flows (European Application 570 612), by the use of continuous gas flows (European Application 640 356) and by the use of special gas mixtures containing NO (European Application 640 357).

Even if the proposed devices and methods operate as intended, they still require the presence of an external source of NO in the treatment room and the use of special safety regulations for staff and monitoring equipment for the patient.

SUMMARY OF THE INVENTION

One object of the present invention is to provide a tracheal tube which makes possible the use of endogenous NO for intubated patients.

Another object of the invention is to provide a device for a ventilator system which makes possible the use of endogenous NO for intubated patients.

The above object is achieved in accordance with the principles of the present invention in a tracheal tube having a proximal end and a distal end adapted to be inserted into the trachea of a patient with the distal end being most deeply inserted (intubation) to conduct, via a flow path between the proximal and the distal end, respiratory gas into the patient's lungs, the tracheal tube having at least one input port disposed a predetermined distance from the distal end of the tracheal tube, so that the exterior of the tracheal tube is connected to the flow path via the input port. The input port permits gas, including endogenously-produced NO, to flow from the upper respiratory tract into the flow path during inspiration by the patient.

By providing the tracheal tube with an input port forming a connection between the outside of the tracheal tube (i.e. the upper respiratory tract when the tracheal tube is inserted into the patient) and the flow path inside the tracheal tube, respiratory gas will be enriched during inspiration with gas containing endogenous NO.

In particular, the connection formed by the input port can be passive or active in its operation; passive when gas from the outside is drawn into the flow path by the gas flow within the flow path and active when the gas from the outside is forced to flow into the flow path.

The above object is also achieved in a ventilator system which has a tracheal tube with a proximal end and a distal end with the proximal end attached to a remainder of the ventilation system for supplying respiratory gas to a patient's lungs, and having a tubular arrangement with a first end adapted to be inserted into at least one of the patient's nostrils and connected to the remainder of the ventilation system for conveying a gas toward the first end during inspiration phases, and wherein the tracheal tube has at least one gas communication path arranged at a predetermined distance from the distal end of the tracheal tube, the gas communication path connecting the exterior of the tracheal tube to a flow path within the tracheal tube.

By the use of a tubular arrangement gas can be supplied to the upper respiratory tract through the nostrils and force gas containing endogenous No down to the tracheal tube in which an opening has been made to pass gas containing endogenous NO into the flow path inside the tracheal tube.

DESCRIPTION OF THE PREFERRED EMBODIMENTS

Figure 1:
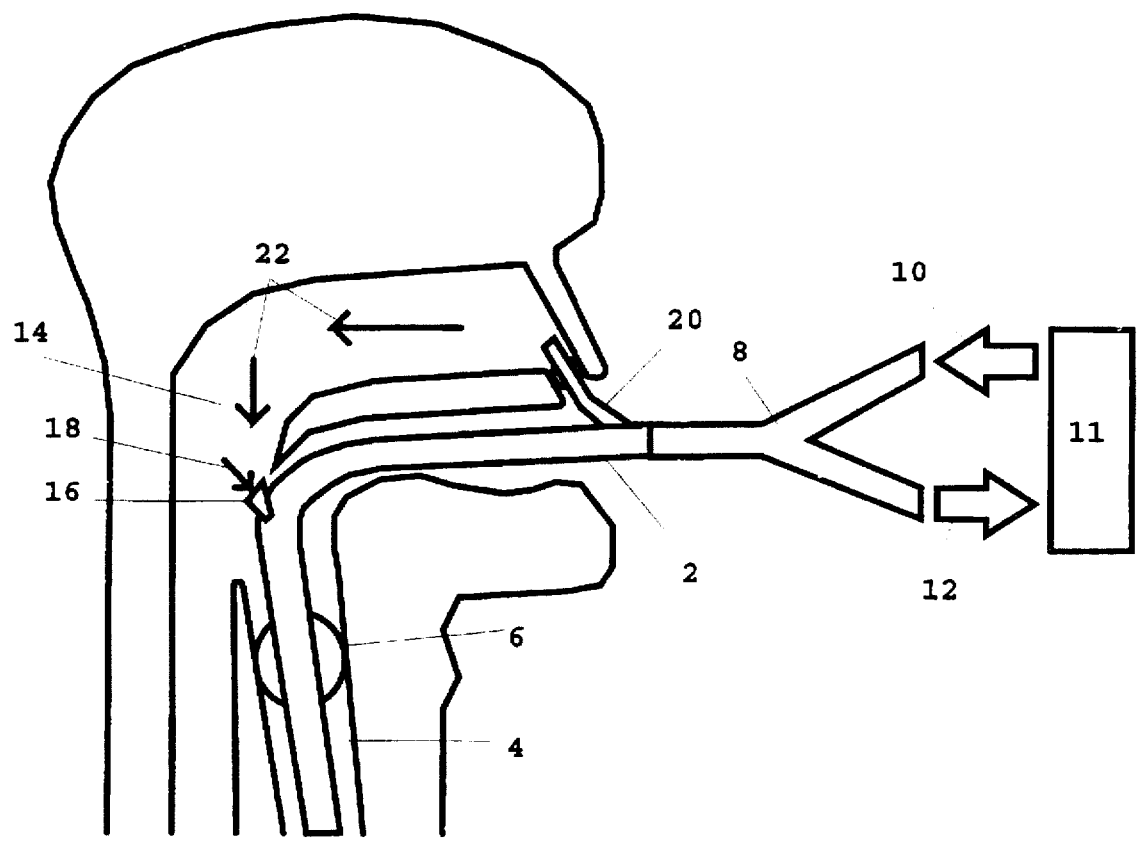
FIG. 1 shows an intubated patient with a tracheal tube/ device according to the invention.

FIG. 1 shows a tracheal tube 2 introduced into a patient's trachea 4 where it is anchored with an inflatable cuff 6. The upper part of the tracheal tube 2 is connected to a Y-piece 8, which is connected to inspiratory and expiratory lines (not shown, but schematically represented by arrows 10 and 12) of a ventilator system. Respiratory gas from a ventilator 11 in the ventilator system is carried to the Y-piece 8 via the inspiration line, as the arrow 10 illustrates. The respiratory gas then flows on to the tracheal tube 2 down into the lower respiratory tract and lungs. During expiration, respiratory gas is carried from the lungs and the lower tracheal tube 2 and via the Y-piece 8 and the expiration line, as the arrow 12 illustrates, back to the ventilator 11.

Endogenous NO is formed/collected/enriched in the patient's upper respiratory tract 14. This endogenous NO is made by the body and in healthy persons, the endogenous NO accompanies inhaled air down into the lungs. This has earlier not been possible for patients receiving respiratory gas from a ventilator 11 via tracheal tubes (including tracheotomy/tracheostomy tubes in certain cases). The tracheal tube 2 is therefore equipped with a input port 16 which is adapted to allow gas containing endogenous NO to flow into the tracheal tube during inspiration, as the arrow 18 illustrates. As a result, endogenous NO is supplied in a manner as similar to natural events as possible. NO gas is only transported a very short distance, so the risk of NO being transformed into NO2 is minimal. Moreover, the NO concentration is regulated by the patient's own body, so no harmful concentrations ever occur. To the contrary, the patient receives the NO concentration to which he or she is accustomed, which may be 0.1 ppm, 10 ppm or some other concentration.

Figure 2:
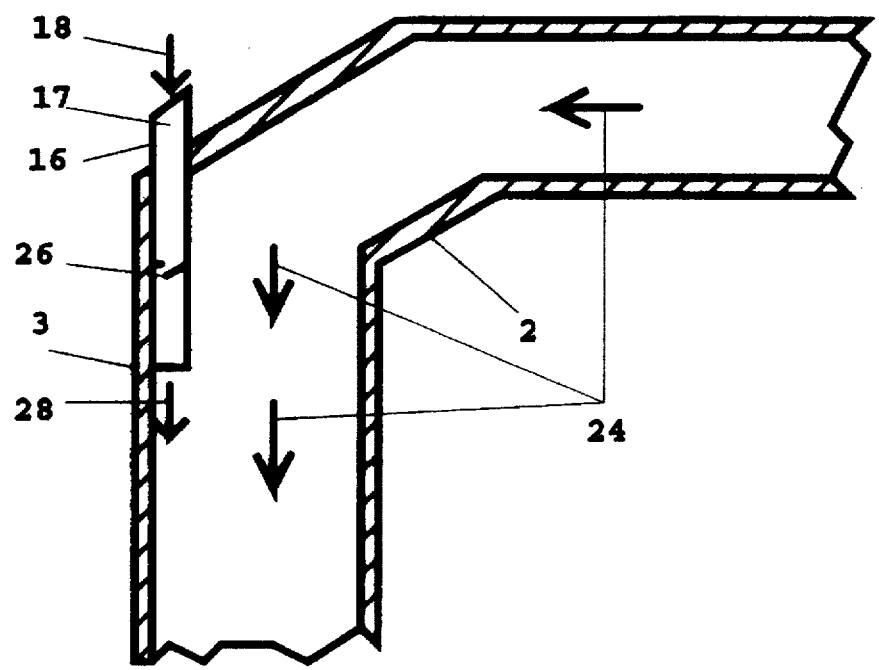
FIG. 2 shows a first embodiment of a input port in the tracheal tube.

FIG. 2 shows a first embodiment of the input port 16. A short tube 17, open at both ends, is arranged in the wall of the tracheal tube 2. When respiratory gas flows through the tracheal tube 2 from the Y-piece 8 during inspiration, as illustrated by the arrows 24, a partial vacuum forms at the opening of the tube 17 into the tracheal tube 2. Gas from upper respiratory tract is accordingly sucked down through the tube 17, into the tracheal tube 2 and accompanies respiratory gas. The arrows 18 and 28 illustrate this action. It is sufficient if only tiny amounts of respiratory gas are carried in the tube 17, for example, 10 to 100 ml is desirable, but larger or smaller quantities can be used, depending on the patient and other circumstances. To prevent respiratory gas from being carried, via the tube 17, to the upper respiratory tract I during expiration, a check (one-way) valve 26 is arranged in the tube 17. The check valve 26 is not necessary to achieve the function of the input port 17, but virtually all modern ventilators measure and monitor expiratory flow. leakage of excessive volumes of gas through the tube 17 could disturb the ventilator's automatic monitoring functions.

Figure 3:
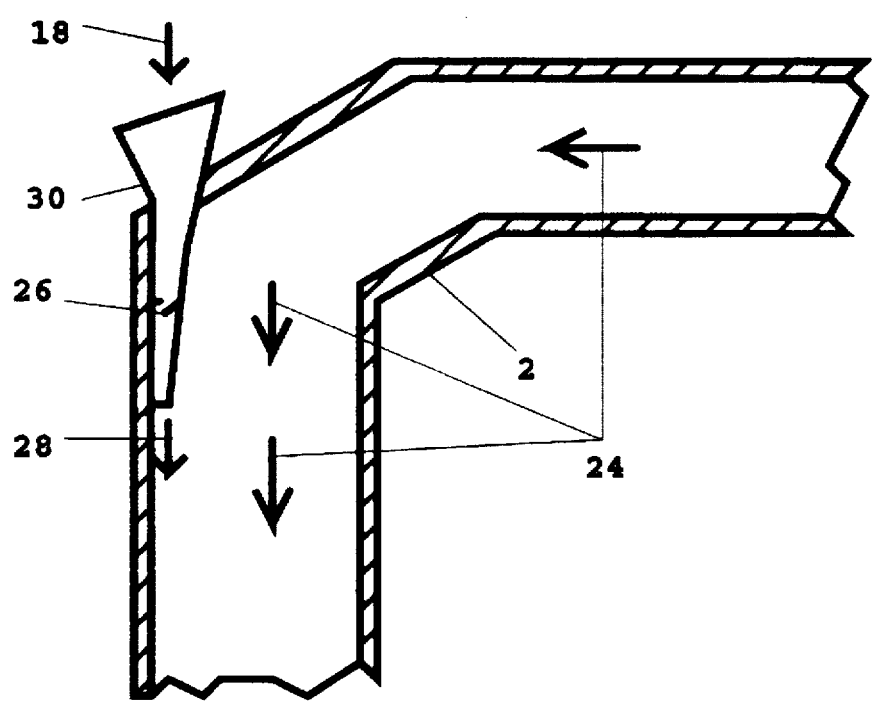
FIG. 3 shows a second embodiment of a input port in the tracheal tube.

A second embodiment of the input port 16 is shown in FIG. 3. Here, the input port 16 has the shape of a funnel 30 with the large opening outside the tracheal tube 2 and the small opening inside the tracheal tube 2. This improves its effect, since a larger partial vacuum can then be generated. At the same time, any backflow through the funnel 30 becomes more difficult, since the resistance to flow at the smaller opening is relatively large. The check valve 26 is virtually unnecessary in this embodiment, but is still retained as a safety precaution. The large mouth of the funnel 30 is located slightly outside the exterior of the tracheal tube 2, i.e. somewhat elevated. This is to reduce the risk of secretions and other body fluids blocking the connection. For the same reason, the tube 17 in FIG. 2 projects from the exterior of the tracheal tube 2.

In FIGS. 2 and 3, only one input port 16 has been arranged in the tracheal tube 2. A number of input ports could be arranged in one tracheal tube to increase the amount of gas containing endogenous NO which is to be added and to increase safety. If any input port becomes obstructed, the others would continue to work.

Figure 4:
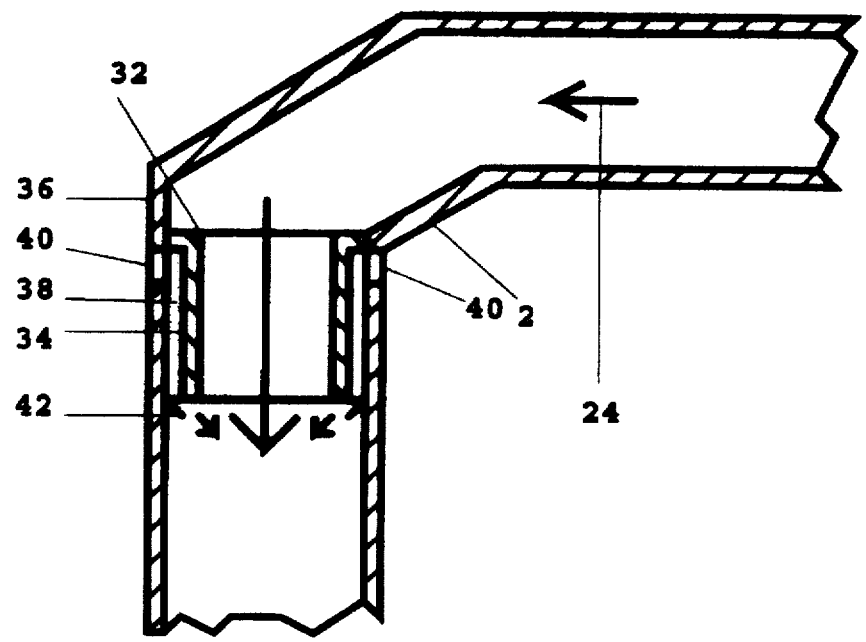
FIG. 4 shows a third embodiment of a input port in the tracheal tube.

A third embodiment of the input port 16 is shown in 35 FIG. 4. A sleeve 32 is arranged in the tracheal tube 2 so the wall 34 of the sleeve 32 and the inner wall 36 of the tracheal tube 2 form a space 38. The upper part of this space communicates with the exterior of the tracheal tube 2 via openings 40, and the lower part communicates with the interior of the tracheal tube 2. The sleeve 32 and the space 38 do not need to be circular nor need they constitute a continuous part of the tracheal tube 2, as shown.

In the same way as described above, gas containing endogenous NO is drawn into the connection (the space 38) and accompanies respiratory gas during inspiration. A thin flap 42 serves as a check valve for the connection. The flow of respiratory gas during inspiration helps keep the flap 42 open, and the flow of respiratory gas during expiration closes the flap 42 against the wall 34 of the sleeve 32.

Figure 5:
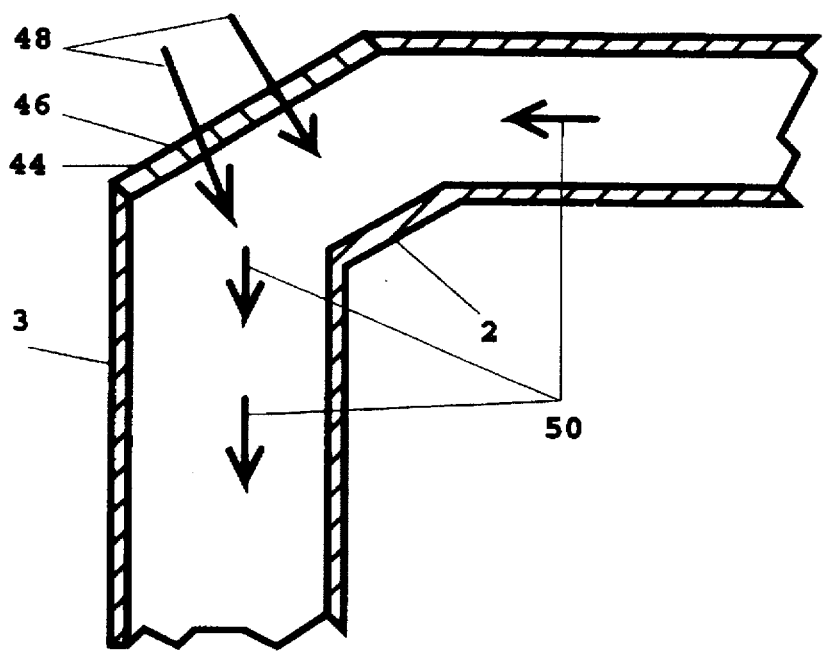
FIG. 5 shows a fourth embodiment of a input port in the tracheal tube.

FIG. 5 shows a fourth embodiment of the input port 16. A membrane 46 is arranged in the tracheal tube's 2 wall 3 and forms an integral part of the tracheal tube 2. The membrane 46 can be thinner or thicker than the wall 3 of the tracheal tube 2 and arranged as an integral sleeve, loop, strip or as some other structure in the wall 3. The design of the membrane 46 depends on e.g. the choice of material.

The membrane 46 is made of a material permeable to NO, such as Teflon®. A material which is only permeable to NO, but not other gases, is ideal. Permeability to oxygen and carbon dioxide in any case preferably should be poor. This is because most ventilator systems have gas meters and analysis systems for these gases.

Figure 6:
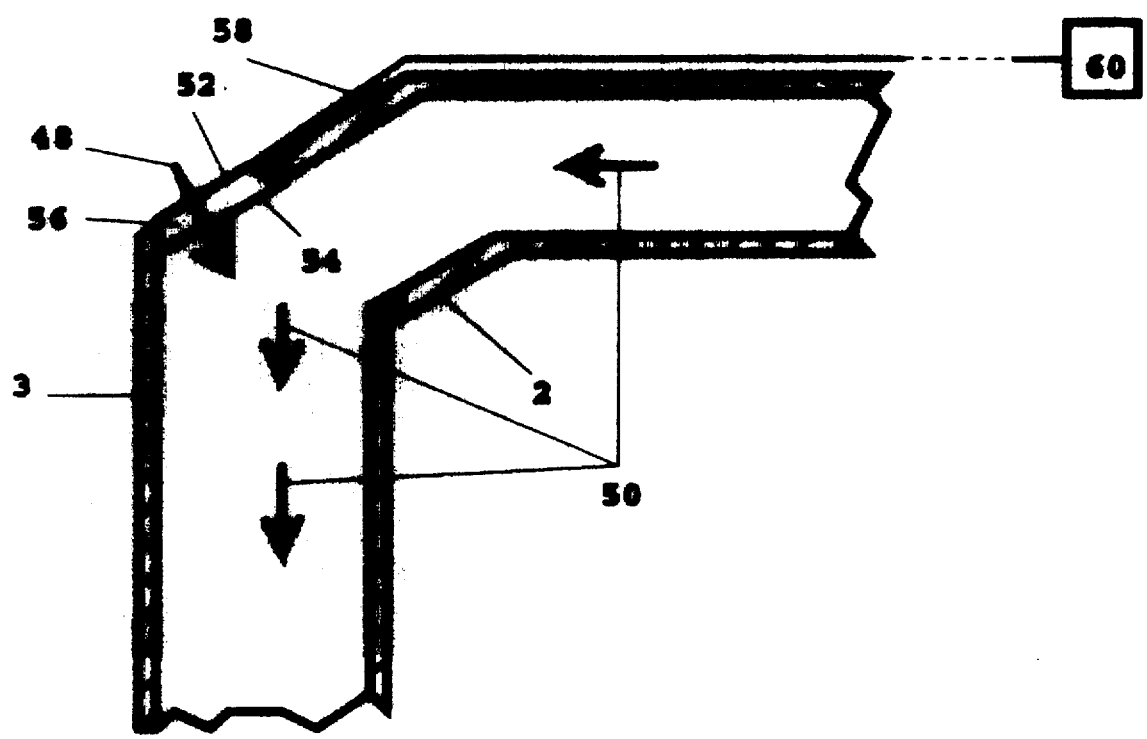
FIG. 6 shows a fifth embodiment of a input port in the tracheal tube.

A fifth embodiment of the input port 16 is shown in FIG. 6. Here, the input port 16 is formed by a micropump 56, an inlet 52 outside the tracheal tube 2 and an. outlet 54 inside the tracheal tube 2. This improves 35 the effect of NO inflow from the upper respiratory tract, since gas is actively pumped into the tracheal tube 2. At the same time, gas is prevented from flowing out of the tracheal tube 21 since the micropump 56 impedes backflow. Suitable micropumps are well-known in the micro-pump art, such as piezoelectric pumps or micro-mechanical silicon 5 pumps. Therefore, a more detailed description of the micropump 56 is not necessary in this context.

The micropump 56 can be regulated via a control line 58 which, in FIG. 6, is shown to run on the outside of the tracheal tube 2, but could just as well run inside the tracheal tube 2 or be integrated into the wall 3 of the tracheal tube 2. When the micropump 56 is controlled by the ventilator in the ventilator system (designated 60 in the figure), the pumping of gas containing endogenous NO can be synchronized with the inspiration phases. This results in a system which simulates the natural supply of endogenous NO as closely as possible.

A number of micropumps 56 can be placed next to each other in order to achieve a large inflow. The pumping of only small amounts of gas by the micropump 56 is sufficient. Pumping from 10 to 100 ml is desirable, but larger or smaller amounts can be suitable, depending on the patient and other circumstances.

The effect of gas supplementation can be enhanced by providing a tubular gas delivery arrangement 20 in the patient's nostril(s), as shown in FIG. 1. A small flow of gas through the nostril/nostrils then sweeps/sweep gas containing endogenous NO down to the tracheal tube 2, as illustrated by the arrows 22. A small increase in pressure in the upper respiratory tract can also enhance the flow of gas through the input port 16. In order to obtain a small increase in pressure, and to avoid flushing the endogenous NO through the patient's mouth, the mouth should be at least partially blocked by using a specific mouth cuff or by taping the mouth around the tracheal tube 2. Surplus gas can, however, be allowed to leak out through the lips around the tracheal tube 2 in order to avoid the build-up of unnecessarily high pressures and to ensure a small flow of gas via the nostrils. In this context, gas added through the tubular arrangement 20 is preferably supplied 5 from a separate source of gas.

Alternatively, the tubular means 20 can be connected to the ventilator system's gas channels, suitably at the tracheal tube 2 or Y piece 8. Part of the respiratory gas is then diverted during inspiration from the larger gas flow passing through the tracheal tube 2. If the patient's lips and mouth are sealed, the total gas volume in the ventilator system and upper respiratory tract can be preserved. The input port 16 can then be devised in a much simpler fashion, e.g., as a number of openings in the tracheal tube 2. Even here, a separate gas source can be connected to the tubular arrangement 20. Positive pressure can then be generated in the upper respiratory tract 14 causing gas containing endogenous NO to be added to the respiratory gas during inspiration.

Figure 7:
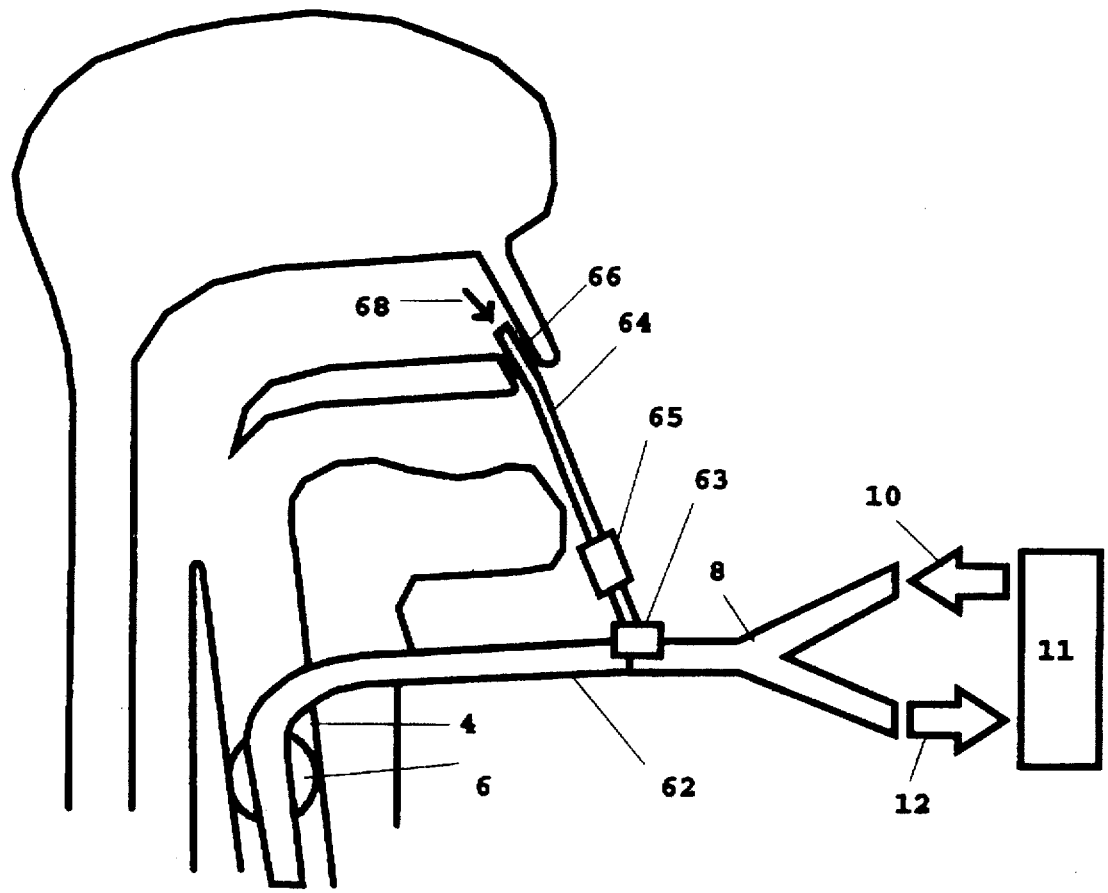
FIG. 7 shows a tracheotomized patient with a tracheal tube/device according to the invention.

FIG. 7 shows a tracheotomy tube 62 inserted into the trachea 4 of a patient and secured by an inflatable cuff 6. The tracheotomy tube 62 is connected to a Y-piece 8 and via this to a ventilator system, basically including inspiration and expiration lines 10 and 12 and a ventilator 11. One end of a tube 64 is inserted into a nostril of the patient and is secured by a further inflatable cuff 66. The tube 64 is a part of a input port, which also includes an ejector device 63 at the other end of the tube 64.

The input port formed by the ejector device 63 and the tube 64 is in this case connected to the Y-piece 8, but could alternatively be connected to the tracheotomy tube 62. The injector device 63 is adapted to draw gas from the upper respiratory tract into the tube 64 and down to the Y-piece 8 by ejector effect when gas flows towards the patient. The ejector effect and ejector devices such as the ejector device 63 are known and need not be described in more detail in this context.

In order to ensure that no gas flows in the wrong direction, 5 check-valves or micro-valves can be included in the input port of FIG. 7.

Instead of the ejector device 63, a micro-pump system 65 could be arranged somewhere along the tube 64 for pumping gas from the upper respiratory tract to the Y-piece. One or several micro-pumps can be used. Again, synchronization with inspiration phases is used. The micro-pumps can be controlled as described above.

All of the described embodiments can be combined where appropriate. For instance, the input port in FIG. 7 can naturally be used with an ordinary tracheal tube, inserted via the mouth or nose of the patient. Micro-valves can replace check-valves and even be used to control communication between the interior and exterior of the tracheal tube so that an open connection between outside and inside of the tracheal tube only exists during inspiration phases.

Although modifications and changes may be suggested by those skilled in the art, it is the intention of the inventors to embody within the patent warranted hereon all changes and modifications as reasonably and properly come within the scope of their contribution to the art.

We claim as our invention:

1. A tracheal tube having a proximal end and a distal end adapted for insertion into a patient's trachea with said distal end conducting, via a flow path between the proximal end and the distal end in the tracheal tube, a respiratory gas to a patient's lungs, said tracheal tube having an input port, said input port comprising means for connecting an exterior of said tracheal tube to said flow path through said input port for causing gas, containing produced endogenously NO by a patient, to flow from a patient's upper respiratory tract into said flow path during inspiration by a patient.

2. A tracheal tube as claimed in claim 1, wherein said input port is disposed a distance from said distal end of said tracheal tube for positioning said input port below the patient's upper respiratory tract when said tracheal tube is inserted into a patient's trachea.

3. A tracheal tube as claimed in claim 1 having a tube wall, said input port comprising an unobstructed tube disposed in said tube wall of said tracheal tube and having a first tube opening and a second tube opening, said first tube opening being disposed outside of said tracheal tube and said second tube opening being disposed in said flow path, facing said distal end of said tracheal tube.

4. A tracheal tube as claimed in claim 3 wherein said unobstructed tube has a predetermined length inside said tracheal tube with at least a portion of said predetermined length extending parallel to said flow path.

5. A tracheal tube as claimed in claim 3 wherein said first tube opening is larger than said second tube opening.

6. A tracheal tube as claimed in claim 5 wherein said unobstructed tube is funnel-shaped.

7. A tracheal tube as claimed in claim 1 having a tube wall with an interior tube wall surface, and wherein said input port comprises an inner wall disposed inside said tracheal tube spaced from said interior tube wall surface and defining a spacing between said inner wall and said interior tube wall surface, said spacing having an upper end communicating through an opening in said tube wall with an exterior of said tracheal tube and having a lower end communicating with the interior of said tracheal tube.

8. A tracheal tube as claimed in claim 1 wherein said input port comprises a nasal tube having a first end adapted for insertion into a patient's nostril and having a second end, an ejector valve means, connecting said second end of said nasal tube to said flow path, for drawing gas via said nasal tube into said flow path when said respiratory gas is conveyed through said tracheal tube.

9. A tracheal tube as claimed in claim 1 wherein said input port comprises flow control means allowing gas to flow from the exterior of said tracheal tube into said flow path and for preventing gas from flowing from said flow path to the exterior of said tracheal tube via said input port.

10. A tracheal tube as claimed in claim 9 wherein said flow control means comprise a one-way valve.

11. A tracheal tube as claimed in claim 1 having tube wall and wherein said input port comprises a NO-permeable membrane disposed in said tube wall between an exterior of said tracheal tube and said flow path and permitting diffusion of NO from the exterior of said tracheal tube into said flow path through said membrane.

12. A tracheal tube as claimed in claim 1 wherein said input port comprises a micropump which pumps gas from an exterior of said tracheal tube into said flow path.

13. A tracheal tube as claimed in claim 12 for use with a ventilation system having a control unit which regulates inspiratory and expiratory phases of said patient, and wherein said micropump is operated by said control unit for activating said micropump in synchronism with each inspiratory phase.

14. A tracheal tube as claimed in claim 13 wherein said control unit activates said micropump for a predetermined period of time at a beginning of each inspiratory phase.

15. A tracheal tube as claimed in claim 11 further comprising means for operating said micropump for pumping a predetermined volume of gas from said exterior of said tracheal tube into said flow path.

16. A ventilation system comprising:
- a tracheal tube having a proximal end and a distal end with a flow path therebetween, said distal end being adapted for insertion into a patient's trachea;
- respiratory assist means, connected to said proximal end of said tracheal tube, for supplying respiratory gas to a patient's lungs;
- a tubular arrangement having a first end adapted for insertion into a patient's nostril for conveying a gas toward said first end during inspiration phases of a patient; and
- said tracheal tube having at least one gas communication path disposed at a predetermined distance from said distal end of said tracheal tube which connects an exterior of said tracheal tube with a flow path within said tracheal tube, said gas communication path causing gas, containing NO endogenously produced by a patient, to flow from a patient's upper respiratory tract into said flow path during inspiration by a patient.

17. A ventilation system as claimed in claim 16 wherein said tubular arrangement is connected to said respiratory-assist means via an opening facing said ventilator.

18. A ventilation system as claimed in claim 16 wherein said tubular arrangement has a second end connected to said proximal end of said tracheal tube.

19. A ventilation system as claimed in claim 16 wherein said tubular arrangement includes a one-way valve which prevents gas from flowing from said first end through said tubular arrangement to said respiratory-assist means.

20. A ventilation system as claimed in claim 19 further comprising at least one micro-valve in said tracheal tube for opening said gas communication path during said inspiration phases.

21. A ventilation system comprising:
- a tracheal tube having a proximal end and a distal end, said distal end being adapted for insertion into a patient's trachea;
- respiratory assist means, connected to said proximal end of said tracheal tube, for supplying respiratory gas to a patient's lungs through said tracheal tube along a respiratory gas path;
- a tubular arrangement having a first end adapted for insertion into a patient's nostril and a second end in communication with said respiratory gas path said gas communication path causing gas, containing NO endogenously produced by a patient, to flow from a patient's upper respiratory tract into said flow path during inspiration by a patient; and
- means for generating a gas flow from said first end of said tubular arrangement to said respiratory gas path during inspiration phases of a patient.

22. A ventilation system as claimed in claim 21 wherein said means for generating a gas flow comprises an ejector device disposed at a second end of said tubular arrangement.

23. A ventilation system as claimed in claim 21 wherein said means for generating a gas flow comprises a micropump disposed for pumping gas through said tubular arrangement.

* * * * *